United States Patent
Wagner-Doebler et al.

(10) Patent No.: US 9,320,682 B2
(45) Date of Patent: Apr. 26, 2016

(54) **TOOTH FILLING MATERIALS AND DENTAL VARNISH FOR INHIBITING THE FORMATION OF A BIOFILM OF *STREPTOCOCCUS MUTANS* AND THE PRODUCTION THEREOF**

(71) Applicants: VOCO Gmbh, Cuxhaven (DE); Helmholtz-Zentrum fuer Infektionsforschung GmbH, Braunschweig (DE)

(72) Inventors: Irene Wagner-Doebler, Evessen (DE); Andree Barg, Otterndorf (DE)

(73) Assignee: VOCO GMBH, Cuxhaven (DE)

( * ) Notice: Subject to any disclaimer, the term of this patent is extended or adjusted under 35 U.S.C. 154(b) by 157 days.

(21) Appl. No.: 13/963,546

(22) Filed: Aug. 9, 2013

(65) Prior Publication Data
US 2014/0051036 A1 Feb. 20, 2014

(30) Foreign Application Priority Data
Aug. 15, 2012 (DE) .......................... 10 2012 214 540

(51) Int. Cl.
| | |
|---|---|
| *A61C 13/08* | (2006.01) |
| *A61C 5/00* | (2006.01) |
| *A61K 6/083* | (2006.01) |
| *A61K 6/00* | (2006.01) |
| *A61K 31/365* | (2006.01) |

(52) U.S. Cl.
CPC .................. *A61K 6/0067* (2013.01); *A61C 5/00* (2013.01); *A61C 13/08* (2013.01); *A61K 6/083* (2013.01)

(58) Field of Classification Search
None
See application file for complete search history.

(56) References Cited

U.S. PATENT DOCUMENTS

| 8,329,674 B2 * | 12/2012 | Yang et al. ........................ 514/62 |
| 8,841,341 B2 * | 9/2014 | Kunze et al. ................... 514/450 |
| 2011/0034708 A1 | 2/2011 | Kunze et al. |
| 2012/0132104 A1 * | 5/2012 | Ruppert et al. ............ 106/15.05 |

FOREIGN PATENT DOCUMENTS

| DE | 102009035970 | 2/2011 | |
| WO | WO 2009014905 A1 * | 1/2009 | ............. A61Q 11/00 |
| WO | 2009030773 | 3/2009 | |
| WO | WO 2009030773 A1 * | 3/2009 | |

OTHER PUBLICATIONS

Abstract of Imazato, Satoshi, "Antibacterial properties of resin composites and dentin bonding systems," Dental Materials, Sep. 2003, vol. 19, No. 9, pp. 449-457.

* cited by examiner

*Primary Examiner* — Peter A Salamon
(74) *Attorney, Agent, or Firm* — Duane Morris LLP; J. Rodman Steele, Jr.; Gregory M. Lefkowitz

(57) ABSTRACT

There are described tooth filling materials and dental varnishes for inhibiting the biofilm formation of *Streptococcus mutans* containing (a) a quantity of an active substance for inhibiting the biofilm formation, (b) a material for forming a structure for the uptake and delayed release of the active substance and (c) a filling material system. Another aspect of this invention relates to a method for producing tooth filling materials or dental varnishes according to the invention for inhibiting the biofilm formation of *Streptococcus mutans*. The present invention also relates to a kit comprising tooth filling materials or dental varnishes according to the invention and one or more additional constituents. There are also described methods for inhibiting the biofilm formation of *Streptococcus mutans*, methods for producing a dental component which inhibits the biofilm formation and the use of the active substance for producing a dental material.

15 Claims, No Drawings

TOOTH FILLING MATERIALS AND DENTAL VARNISH FOR INHIBITING THE FORMATION OF A BIOFILM OF *STREPTOCOCCUS MUTANS* AND THE PRODUCTION THEREOF

The present invention relates to tooth filling materials and dental varnishes for inhibiting the formation of a biofilm of *Streptococcus mutans*, containing (a) a quantity of an active substance for inhibiting the formation of a biofilm, (b) a material for forming a structure for the uptake and delayed release of the active substance and (c) a filling material system. Another aspect of this invention relates to a method for producing tooth filling materials or dental varnishes according to the invention for inhibiting the formation of a biofilm of *Streptococcus mutans*. The present invention also relates to a kit comprising tooth filling materials or dental varnishes according to the invention and one or more additional constituents. There are also described methods for inhibiting the formation of a biofilm of *Streptococcus mutans*, methods for the production of a dental component which inhibits the biofilm formation and the use of the active substance specified in greater detail below for producing a dental material.

Additional aspects of the present invention will become apparent from the following description and in particular from the patent claims appended.

The infectious disease, caries, which is the most widespread among humans occurs in the form of caries lesions when biofilm bacteria (plaque bacteria), primarily *Streptococcus mutans* and Lactobacillaceae, form organic acids due to the fermentation of fermentable carbohydrates by means of an anaerobic substance metabolism. The acids diffuse into the hard tooth tissue and destroy the crystalline phases of the enamel and the dentine. Owing to the dissolution of those minerals, structural changes are caused in the hard tooth tissue. This demineralisation takes place from a pH value of less than 5.5. Furthermore, a continuous precipitation of specific ions occurs from the saliva, such as calcium and phosphate ions. The presence of those ions in the oral cavity results in remineralisation. If fluoride is present, the remineralisation is further promoted by acid-resistant fluorohydroxyapatite being formed. In the dynamic milieu of the oral cavity, demineralisation and remineralisation alternate. If there is an equilibrium between those processes, caries lesions are not formed. If the equilibrium is disturbed, however, the formation of a caries lesion is promoted owing to the increasing loss of inorganic constituents of the enamel.

This equilibrium between demineralisation and remineralisation is disturbed by biofilms which form on the boundary between the tooth surface (these also include synthetic surfaces such as fillings or dental prostheses) and the remainder of the oral cavity. Biofilms comprise a thin mucous layer or a thin mucous film, in which microorganisms (for example, bacteria such as *Streptococcus mutans*) are embedded. In addition to the microorganisms, biofilms mainly contain water and the extra-cellular polymeric substances excreted by the microorganisms, such as, for example, polysaccharides (for example, dextrane, alginate or cellulose), proteins, lipids, and nucleic acids, which form hydrogels so that a mucous matrix is produced in which additionally nutrients and other substances may be dissolved.

In addition to the effect that biofilms disturb the equilibrium between demineralisation and remineralisation, the demineralisation of the hard tooth tissue is further increased by organic acids which occur owing to anaerobic metabolism of fermentable carbohydrates by the microorganisms in the biofilm. In dentistry, combatting biofilms is an important aspect which is becoming increasingly significant. Combatting biofilms by application of antibiotics has two fundamental problems. First, bacteria form resistance against antibiotics which allows the bacteria to weaken or to completely neutralise the action of antibiotically active substances and, second, the application of the antibiotics is problematic. The oral application of antibiotics does not result in a sufficiently high concentration of antibiotics in the tooth enamel whereas the use of antibiotic mouthwashes only combats bacteria in the outer biofilm layer.

Consequently, there is a constant need for actions to be taken and means which inhibit the formation of biofilms in the oral cavity and which combat biofilms at the locations where they occur, in particular on the tooth surface (these also include synthetic surfaces such as fillings or dental prostheses).

The inhibition or the avoidance of biofilm formation can be achieved not only by the use of antibiotic substances but also by other actions to be taken. Thus, for example, the use of protein-repellent or hydrophobically coated surfaces of the dental materials is possible. The growth or adhesion of the bacteria on the dental materials is thereby made harder.

The use of quaternary ammonium salts as antimicrobial additives has been known for some time. Thus, for example, a silane having quaternary ammonium groups as the functional group is produced by the company Microshield and marketed for equipping filters, textiles and wound dressings with antibacterial activity. GB 1 433 303 A describes filler particles for plastic materials and discloses that they are silanised and coated with quaternary ammonium salts. Diatomaceous earths processed in that manner or pyrogenic silicic acids are proposed, for example, for use in wood coatings, sealing masses, catheters or textile fibres.

According to DE 10 2009 035 970 document JP 10025218 A discloses inorganic filler materials which are coated with a polymeric coating containing antimicrobial groups. The coating is produced by polymerisation of corresponding (meth)acrylate monomers which carry phosphonium or quaternary ammonium groups.

According to DE 10 2005 042 078 A1, dental filler particles are coated with antimicrobially active polysaccharides. Such fillers coated with a polysaccharide are enveloped with another polymer (page 4, paragraph 0034). In addition a CC double bond is introduced into the polysaccharide chitosan in order to ensure polymerisation to the polymer (page 4, paragraph 0037). Triclosan is accordingly covalently bonded on the surface of the filling material (page 5, paragraph 0047).

DE 10 2009 035 970 A1 describes dental materials which contain at least one antimicrobially active substance which is applied to organic particles or organic polymer beads and which is bonded to the particles or polymer beads in a non-covalent manner. The antimicrobially active substance is an iminopyridinium derivative, octenidine salt, dequalinium salt, sanguinarine, Akacid®, chlorohexidine, alexidine, hexetidine, cetylpyridinium chloride, benzalkonium chloride, octenidine dihydrochloride or triclosan.

In US 2012/0095114 A1, triclosan derivatives are covalently bonded to monomers and oligomers and subsequently used to form substrates which can be applied to dental products. U.S. Pat. No. 6,207,139 describes various dental products which contain triclosan and which exhibit an anti-tartar effect.

Benzimidazole derivatives are used in US 2012/0171129 A1 in order to remove or to inhibit biofilms or to prevent the formation of biofilms. The use of the described benzimidazole derivatives inter alia in dental floss, toothpaste or chewing gum is also described.

WO 2004/078154 describes dental care compositions which contain particles. Those particles inhibit or prevent the formation of bacteria on oral surfaces and on compositions which contain those particles.

It was a primary object of the present invention to provide a tooth filling material or a dental varnish for inhibiting the formation of biofilms of *Streptococcus mutans* which achieve a degree of biofilm inhibition which is better than that of an otherwise identically composed tooth filling material or dental varnish comprising one of the compounds, chlorohexidine and triclosan, used in the dental sector as antimicrobially active substances.

This object is achieved by tooth filling materials or dental varnishes for inhibiting the formation of biofilms of *Streptococcus mutans* comprising:

(a) a quantity of one or more compounds of the formula (I) as the active substance for inhibiting the formation of biofilms of *Streptococcus mutans*

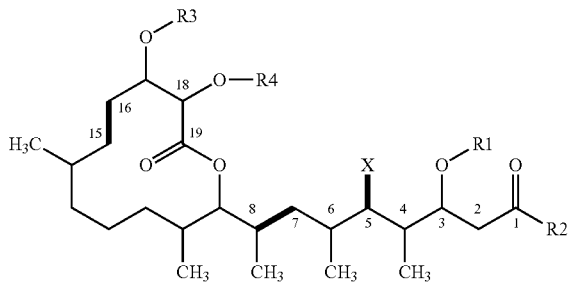

(I)

where, in one compound or, independently of each other, in each of the plurality of compounds of the formula (I), R1, R2, R3 and R4 represent independently of each other hydrogen, a branched or unbranched alkyl group with 1 to 12 carbon atoms, preferably methyl, ethyl, n-propyl, isopropyl, n-butyl, isobutyl, n-heptyl, isoheptyl, n-pentyl, isopentyl, n-hexyl or isohexyl, or a branched, unbranched or cyclical, saturated, unsaturated or aromatic hydrocarbon substitute with 7 to 12 carbon atoms or aryl, aryl alkyl or an additional aromatic group, X represents O or OH and where the boldly emphasised lines between the carbon atoms 7 and 8 and between the carbon atoms 15 and 16 represent a single bond or a double bond independently of each other and where the boldly emphasised line between the carbon atom 5 and the group X bonded thereto, in case that X represents OH, represents a single bond and, in case that X represents O, represents a double bond and (b) a material for forming a structure for the uptake and delayed release of the active substance comprising one, two, three or more polymerisable monomers, and (c) one or more particulate fillers and (d) one or more additives selected from the group comprising initiators, accelerators and inhibitors.

The numbering of the carbon atoms relates to the numbers as indicated in the above formula.

Tooth Filling Materials or Dental Varnishes—One-Component and Two-Component Systems:

In dental practice, a distinction is made between tooth filling materials or dental varnishes inter alia in accordance with the type of hardening thereof, which may be carried out by light polymerisation and/or autopolymerisation (light hardening and/or chemical hardening). Light-hardenable tooth filling materials or dental varnishes which are available in the form of one-component materials are, in comparison with tooth filling materials or dental varnishes which are available in the form of a component of a two-component system, are generally less susceptible to application errors because one-component materials are not freshly mixed before use and consequently there also cannot be any bubble formation during the mixing, as often occurs in two-component systems. Light-hardenable one-component tooth filling materials or dental varnishes are consequently often preferred. Besides one-component light-hardenable tooth filling materials or dental varnishes and two-component autopolymerisable tooth filling materials or dental varnishes (chemically hardenable, non-light-hardenable), there are also known so-called dual-hardening, two-component systems which can be hardened by light-hardening and chemical hardening.

Tooth filling materials or dental varnishes according to the invention are preferably light-hardening one-component systems but, in individual cases, a formulation is preferred in which tooth filling materials or dental varnishes according to the invention are formulated as a component of a two-component system, the two-component system being a chemically hardening (non-light-hardening) system or a dual-hardening system. After a two-component system has been mixed, an admixture of those components is present, with the admixture being a tooth filling material according to the invention or a dental varnish according to the invention.

Component (a) Active Substance—Compound of Formula (I):

In general, any compounds of the formula (I) as defined above (and their admixtures) may be used as component (a), that is to say, as the active substance.

However, tooth filling materials or dental varnishes according to the invention are preferred in which a compound of the formula (I) or a plurality of compounds of the formula (I)

(i) has a double bond between the carbon atoms 15 and 16 and/or (ii) has a double bond between the carbon atoms 7 and 8 and/or (iii) has a carboxyl group at the carbon atom 5, where the numbering of the carbon atoms relates to the numbers indicated in the above structure. The options (i), (ii) and (iii) may be met independently of each other.

Tooth filling materials or dental varnishes according to the invention are particularly preferred in which the compound of the formula (I) or one or more of the compounds of the formula (I) have a double bond between the carbon atoms 15 and 16, a double bond between the carbon atoms 7 and 8 and a carboxyl group at the carbon atom 5, where the or one or more of the compounds of the formula (I) are preferably substituted by hydrogen at R3 and R4 and R1 and R2 represent independently of each other hydrogen, a branched or unbranched alkyl group with 1 to 12 carbon atoms, preferably methyl, ethyl, n-propyl, isopropyl, n-butyl, isobutyl, n-heptyl, isoheptyl, n-pentyl, isopentyl, n-hexyl or isohexyl, or a branched, unbranched, or cyclical, saturated, unsaturated or aromatic hydrocarbon substitute with 7 to 12 carbon atoms or aryl, arylalkyl or another aromatic group.

There are particularly preferred tooth filling materials or dental varnishes according to the invention in which the one compound having the formula (I) or one of the plurality of compounds having the formula (I) is carolacton of the formula (II)

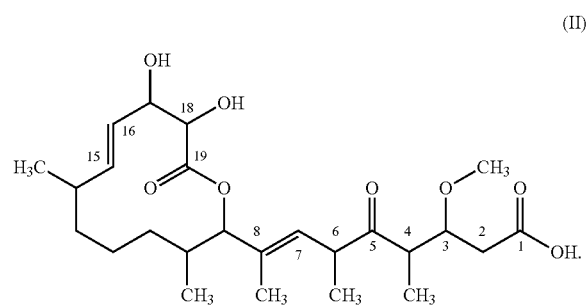 [SMILES: COC(CC(=O)O)C(C)C(=O)C(C)/C=C(\C)C1OC(=O)C(O)C(O)/C=C/C(C)CCCC1C]

The use of compounds of the formula (I) and in particular carolacton as a biofilm inhibitor is already described in WO 2009/030773 A10. There are particularly disclosed pharmaceutical compositions which inhibit the biofilm formation, whereas the biofilms are formed, for example, on tooth surfaces in the form of dental plaque. However, tooth filling materials or dental varnishes according to the invention are not described, in particular no admixtures which comprise one of the components (b) or (c) of a tooth filling material or dental varnish according to the invention are disclosed. WO 2009/030773 A10 also does not disclose any compositions or admixtures which are suitable as a tooth filling material or dental varnish.

The production of compounds of the formula (I) and carolacton of the formula (II) is disclosed in WO 2009/030773 A10, cf. in particular Example 1 therein.

In our own research relating to the antimicrobial action of triclosan, chlorohexidine and carolacton in relation to *Streptococcus mutans*, it has been found for solutions of those active substances that triclosan and chlorohexidine also have a very powerful antimicrobial activity at specific low concentrations, whilst carolacton only has a weak antimicrobial action at the same concentration (see in this regard Example 8). The antimicrobial action of carolacton with respect to *Streptococcus mutans* is consequently weaker than the antimicrobial action of the compounds chlorohexidine and triclosan used as antimicrobial active substances in the dental sector. Therefore, it is particularly surprising that, when tooth filling materials or dental varnishes according to the invention are used with carolacton, the biofilm inhibition is substantially better than with the use of corresponding tooth filling materials or dental varnishes which contain chlorohexidine or triclosan in place of carolacton (see in this regard Example 9).

Similar results were obtained with compounds of the formula (I) which are not carolacton of the formula (II); among those compounds, particularly good results were achieved with compounds of the formula (I) in which R3 and R4 each represent hydrogen.

Component (b)—Material for Forming a Structure for the Uptake and Delayed Release of the Active Substance The tooth filling materials or dental varnishes according to the invention for inhibiting the biofilm formation of *Streptococcus mutans* comprise as the component (b) a material for forming a structure for the uptake and delayed release of the active substance comprising one, two, three or more polymerisable monomers.

The polymerisable monomers preferably comprise at least one ethylene group such as, for example, the (meth)acrylates and (meth)acrylamides generally used in dental chemistry in composite materials.

Tooth filling materials or dental varnishes according to the invention are preferred in which the one polymerisable monomer or one, two, three, a plurality of or all the plurality of polymerisable monomers of the component (b) is/are selected from the group of (meth)acrylates and (meth)acrylamides, is/are preferably selected from the group comprising ethylene glycol dimethacrylate (EGDMA), 1,6-hexanediol dimethacrylate (HEDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, triethylene glycol dimethacrylate (TEGDMA), urethane dimethacrylate (7,7,9-trimethyl-4,13-dioxo-3,14-dioxa-5,12-diazahexadecan-1,16-dioxy-dimethacrylate (UDMA)), glycerol dimethacrylate (GlyDMA), bisphenol-A-glycidyl-methacrylate (Bis-GMA), 1,12-dodecandiol dimethacrylate (DODMA), hydroxyethyl methacrylate (HEMA), polyethylene glycol dimethacrylate (PEGDMA) and ethoxylated bisphenol-A-dimethacrylate (EtoBG).

As already described above, tooth filling materials or dental varnishes are hardened in dental practice by light and/or autopolymerisation (light hardening and/or chemical hardening). In the context of the present invention, tooth filling materials or dental varnishes according to the invention are particularly preferred in which one polymerisable monomer or one, two, three, a plurality of or all the plurality of the polymerisable monomers are radically or non-radically polymerisable, preferably radically or non-radically polymerisable by a light-induced reaction and/or catalysed reaction. Tooth filling materials or dental varnishes in which the one polymerisable monomer or one, two, three, a plurality of or all the plurality of the polymerisable monomers are radically polymerisable by a light-induced reaction, are often preferred in practice. Such preferred tooth filling materials or dental varnishes are preferably light-hardening one-component systems, but in individual cases a formulation is preferred in which tooth filling materials or dental varnishes according to the invention are formulated as a component of a two-component system, the two-component system being a dual-hardening system.

In patent literature, diesters of the acrylic acids or methacrylic acids are often mentioned as polymerisable monomers (for example, also in DE 39 41 629 A1, which is incorporated in the present application by way of reference, in particular the disclosure in the region of column 6, line 15 to column 8, line 10); they are particularly suitable for use as a polymerisable monomer in tooth filling materials or dental varnishes according to the invention.

Preferred polymerisable monomers are hydroxyl compounds which comprise at least one ethylene double bond. All the hydroxyl compounds of acrylates or methacrylates generally used in dental chemistry may be used. Preferred are hydroxyl compounds of methacrylates, again preferably 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol dimethacrylate, glycerol dimethacrylate and 2,2-bis[4-[3-methacryloyloxy-2-hydroxypropoxy]phenyl]-propane.

The polymerisable monomers mentioned may be used individually or in admixtures.

Component (c)—Particulate Fillers

The tooth filling materials or dental varnishes according to the invention for inhibiting the biofilm formation of *Strepto-*

*coccus mutans* comprise as component (c) one or more (chemically different) particulate fillers.

The term particulate fillers is intended to refer to fillers which are in the form of particles. The particles (particulates) may be of any form; the term "particulate fillers" consequently comprises in particular shape-independent solid materials, fibres, tubes and also "doughnuts" (that is to say, annuluses), "multi-dimples", toroidal, compact and porous, isolated and aggregated/agglomerated solid materials.

In accordance with the manufacturing method of the particulate fillers, the particles may be present in partially agglomerated or aggregated form.

The particulate fillers may be chemically uniform (that is to say, all have the same chemical composition) or be used as an admixture of chemically different fillers. In order to optimise the product properties, the particulate fillers may be introduced into the recipes in various grain sizes. The fillers or the admixture of a plurality of chemically different fillers may have a unimodal or polymodal distribution, for example, a bimodal distribution.

Suitable inorganic particulate fillers are, for example, amorphous materials on the basis of mixed oxides comprising $SiO_2$, $ZrO_2$ and/or $TiO_2$, microfine fillers such as pyrogenic and/or non-agglomerated and/or non-aggregated silicic acid or precipitated silicic acid and macro- or mini-fillers such as quartz dental glass or powdered glass, barium silicate glasses, barium fluorosilicate glasses, strontium silicate glasses, strontium borosilicate, Li/Al-silicate glasses, barium glasses, calcium silicates, sodium aluminium silicates, fluoroaluminium silicate glasses, oxides of aluminium or silicon, zeolites, apatite, zirconium silicates, weakly-soluble metal salts such as barium sulphate or calcium fluoride and x-ray-opaque fillers such as ytterbium fluoride.

For better incorporation in the structure resulting from component (b) for the uptake and delayed release of the active substance (the polymer matrix), the particulate fillers may be surface-modified. The organic surface treatment of the fillers generally improves the compatibility of the particle surface with the organic binder phase because the particle surface which is hydrophilic per se is made hydrophobic by the surface treatment and is then more compatible with the plastics matrix. The surface modification is preferably carried out in such a manner that the inorganic surface is covalently bonded to the resultant polymer by copolymerisation during hardening of the material. The inorganic surface is often silanised. In this instance, pre-hydrolysed methacryloxy alkyl trialkoxysilanes are used, such as, for example, 3-methacryloxy propyl trimethoxysilane, in which the silanol groups formed during hydrolysis react with the free hydroxyl groups of the filler surface. Information concerning modification reagents and execution methods are known inter alia from DE 24 05 578 A1, US 2002/0065337, DE 195 08 586 A1, WO 00/69392 and U.S. Pat. No. 6,387,981.

The production of nano-scale metal and heavy metal oxides and mixed oxides is possible with sol gel methods.

According to a preferred method for producing colloidal silica sol, water glass is taken as the starting point. In this instance, an aqueous solution of sodium silicate is deionised by means of an ion exchanger, whereby silicic acid is formed. That acid is unstable and polymerises to form small particles from which the nano-scale silicic acids are then formed. In this instance, narrow distributions of particle sizes can also be obtained by the process parameters being adjusted suitably.

Similarly flame-hydrolytically produced pyrogenic silicic acids which are commercially available in different particle sizes via the product ranges "Aerosile" (Degussa) or "CAB-O-SIL" (Cabot Corporation), the silicic acids produced according to alternative methods can also be commercially obtained in different sizes via the product ranges "Highlink" (Clariant), "Nalco" (Nalco Chemical Company), "Nanocryl" (Nanoresins), "Bidzil" (Eka Chemicals), "Levasil" (Messrs. H.C. Starck), "NexSil" (Nyacol) or "Ludox" (du Pont).

In order to adjust the rheology, tooth filling materials or dental varnishes according to the invention may contain different silicic acids, preferably pyrogenic and/or non-agglomerated and/or non-aggregated silicic acids.

There are particularly preferred tooth filling materials or dental varnishes according to the invention comprising in or as component (c) one or more inorganic particulate fillers, the one or one or more or all of the inorganic particulate fillers preferably being selected from the group comprising silanised $SiO_2$ nanoparticles, pyrogenic and/or non-agglomerated and/or non-aggregated silicic acids, non-aggregated, non-agglomerated $SiO_2$ nanoparticles, dental glass particles, silanised dental glass particles, zirconium oxide particles, aluminium oxide particles and inorganic filler particles surface-modified by means of organic structural elements.

Component (d)—Initiators, Accelerators and Inhibitors

Tooth filling materials or dental varnishes according to the invention comprise one or more additives selected from the group comprising initiators, accelerators and inhibitors, that is to say, additives which allow or support (i) light-hardening and/or (ii) chemical hardening of the one or more polymerisable monomers. Additional additives may be used in addition to those additives.

Examples of additives which allow or support light-hardening of the one or more polymerisable monomers are catalysts which only act in a photo-sensitising manner (photosensitisers, photoinitiators) and accelerators (triggers, co-initiators) which are preferably used in combination with photosensitisers.

Examples of suitable photosensitisers are alpha-diketones (for example, camphor quinone), benzoin alkyl ether, thioxanthones, benzophenones, acetophenones, ketals, titanocenes, sensitising colouring substances, etc. The sensitisers may be used alone or in combination. Specific substance examples of the different classes appear, for example, in DE 10 2006 019 092 A1 or in DE 39 41 629 C2, which are incorporated in the present application by reference.

Examples of specific accelerators which are used together with the photosensitisers are tertiary amines (for example, ethyl-p-N,N-dimethylamino benzoate (DABE)), secondary amines, barbituric acids, tin compounds, aldehydes and sulphur compounds. Specific substance examples of the different classes appear, for example, in DE 10 2006 019 092 or in DE 39 41 629 C2, which are incorporated in the present application by reference.

Additional suitable additives (initiators and initiator combinations) are described in DE 601 16 142 which is incorporated in the present application by reference.

The photoinitiators which can be used in the context of the present invention are preferably characterised in that they can harden tooth filling materials or dental varnishes according to the invention by absorption of light in the wavelength range from 300 nm to 700 nm, preferably from 350 nm to 600 nm and particularly preferably from 380 nm to 500 nm, optionally in combination with one or more co-initiators.

The absorption maximum of camphor quinone (CC) is approximately 470 nm and is consequently in the range of blue light. Camphor quinone (CC) is included among the $PI_2$ initiators and is regularly used together with a co-initiator.

Tooth filling materials or dental varnishes according to the invention preferably contain the combination of an alpha-diketone and an aromatic tertiary amine, and the combination of camphor quinone (CC) and ethyl-p-N,N-dimethylamino benzoate (DABS)) is preferred.

It is also preferable to have the additional combination of the "alpha-diketone/aromatic tertiary amine" system with a phosphinoxide, in particular with phenyl-bis(2,4,6-trimethylbenzoyl)phosphinoxide and/or 2,4,6-trimethylbenzoyl-diphenylphosphinoxide. With regard to the structures of suitable phosphinoxides for use in a composition according to the invention, reference is made to the publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2 which are incorporated in the present application by reference.

The phosphinoxides set out in these publications are particularly suitable alone or in combination with the "alpha-diketone/amine" system as a photopolymerisation initiator system in the tooth filling materials or dental varnishes according to the invention.

Alternatively, it is also possible to use borate salts as photoinitiators, as described, for example, in U.S. Pat. No. 4,772,530, U.S. Pat. No. 4,954,414, U.S. Pat. No. 4,874,450, U.S. Pat. No. 5,055,372 and U.S. Pat. No. 5,057,393.

Additional suitable photoinitiators in the context of the present invention are described in J.-P. Fouassier, Photoinitiation, Photopolymerization and Photocuring, Hanser Publishers, Munich, Vienna, N.Y. 1995 and in J. F. Rabek (Hrsg.), Radiation Curing in Polymer Science and Technology, Vol. II, Elsevier Applied Science, London, N.Y. 1993, which are incorporated in the present application by reference.

The person skilled in the art knows various initiators for chemical hardening which can also be used in the context of the present invention. By way of example, reference is made to EP 1 720 506 in this regard.

Preferred initiators for chemical hardening of tooth filling materials or dental varnishes according to the invention are benzoyl peroxide, lauroyl peroxide and dibenzoyl peroxide. The chemical initiators mentioned, in particular dibenzoyl peroxide, are preferably used in combination with amines, such as, for example, N,N-dimethyl-p-toluidine, N,N-dihydroxyethyl-p-toluidine and structurally related amines.

The peroxides and amines are generally divided between two different components of a dental material, with both components and the admixture present after the components are mixed preferably being tooth filling materials or dental varnishes according to the invention. When the amine-containing component (so-called base paste) is mixed with the peroxide-containing component (so-called initiator or catalyst paste), the radical reaction is initiated owing to the reaction of the amine and peroxide (redox reaction).

Dual-hardening systems are both chemically hardenable and light-hardenable systems which generally comprise two components, wherein preferably both components as well as the admixture present after mixing the components are tooth filling materials or dental varnishes according to the invention. Dual-hardening systems comprise a combination of photo initiators and initiators for chemical hardening.

For example, the base paste of a dual-hardening system may be a tooth filling material according to the invention or dental varnish according to the invention and further contain a photoinitiator in addition to an amine-containing component so that the base paste can be used either alone as a light-hardening dental material or together with the initiator paste as a light-hardening and chemically hardening dental material.

Alternatively or additionally to the peroxide/amine systems, there may be used in chemically hardening systems in the context of the present invention redox systems which comprise barbituric acids or barbituric acid derivatives and/or malonyl sulphamides.

Among the barbituric acid systems, the so-called "Bredereck systems" are of great importance. Examples of suitable "Bredereck systems" and references to the corresponding patent literature are given in EP 1 839 640 and in DE 14 95 520, WO 02/092021 or in WO 02/092023.

Suitable malonyl sulphamides are in EP 0 059 451. Preferred compounds are 2,6-dimethyl-4-isobutyl malonyl sulphamide, 2,6-diisobutyl-4-propyl malonyl sulphamide, 2,6-dibutyl-4-propyl malonyl sulphamide, 2,6-dimethyl-4-ethyl malonyl sulphamide and 2,6-diocytyl-4-isobutyl malonyl sulphamide.

Furthermore, sulphur compounds in the oxidation stage +2 or +4 may be used such as sodium benzene sulphinate or sodium paratoluol sulphinate.

In order to accelerate the hardening, the polymerisation may be carried out in the presence of heavy metal compounds such as Ce, Fe, Cu, Mn, Co, Sn or Zn, with copper compounds being particularly preferred. The heavy metal compounds are preferably used in the form of soluble organic compounds. Preferred copper compounds are copper benzoate, copper acetate, copper ethyl hexanoate, copper di(methacrylate), copper acetyl acetonate and copper naphthenate.

The tooth filling materials or dental varnishes according to the invention preferably contain one or more inhibitors, also referred to as stabilisers. Those are added to an admixture in order to prevent spontaneous polymerisation. They react with prematurely occurring radicals which are intercepted, prevent premature polymerisation and increase the storage stability of the light-hardenable composition. Common inhibitors are phenol derivatives such as hydroquinone monomethyl ether (HQME) or 2,6-di-tert.butyl-4-methyl phenol (BHT). Other inhibitors such as 2,2-diphenyl-1-picrylhydrazyl-, galvinoxyl-, triphenyl methyl-radicals, 2,3,6,6,-tetramethyl piperidinyl-1-oxyl radicals (TEMPO) and derivatives of TEMPO or phenothiazine and derivatives of that compound are described in EP 0 783 880 B1, which are incorporated in the present application by reference. Alternative inhibitors are set out in DE 101 19 831 A1 or in EP 1 563 821 A1, which are incorporated in the present application by reference.

Component (e)—Metal Additives

A tooth filling material according to the invention or dental varnish according to the invention preferably comprises one or more additives selected from the group comprising silver, substances releasing silver ions, copper, substances releasing copper ions, zinc and substances releasing zinc ions. Those additives may be used in addition to other additives and are generally used in order to still further improve the antimicrobial action of the tooth filling materials or dental varnishes according to the invention and to even better inhibit the biofilm formation.

Component (f)—Softeners

In the context of the present text, the term "softeners" refers to not further polymerisable polymers which do not take part in a radical polymerisation with (meth)acrylates and which can be used for the purpose of a so-called "external softening". For example, polyethylene glycol (PEG) is a softener in the sense of this definition.

In our own research, it has been found that in some cases the presence of softeners (as defined above) in tooth filling materials or dental varnishes according to the invention has a positive influence on the controlled release of the active substance of the component (a). Softeners which are strongly hydrophilic and which can therefore absorb the active substance in a particularly controlled manner and release it in a controlled manner are particularly preferred.

Therefore, tooth filling materials or dental varnishes according to the invention are particularly preferred comprising as component (f) one, two, three or more softeners, preferably polyethylene glycol as the softener.

Therefore, tooth filling materials or dental varnishes according to the invention are particularly preferred, with a total of from 0% by weight to 25% by weight, preferably from 0.01% by weight to 15% by weight, particularly preferably from 0.1% by weight to 5% by weight of a softener being contained in relation to the total weight of the tooth filling material or dental varnish.

Component (g)—Other Constituents

Tooth filling materials or dental varnishes according to the invention preferably comprise one or more additives which are not substances which can already be included as a constituent of one of the above-discussed components. Such constituents are referred to as "other constituents".

Thus, for example, UV absorbers which are capable, for example, owing to their conjugated double bonding systems and aromatic rings, of absorbing UV radiation may be a constituent of a tooth filling material or dental varnish according to the invention. Examples of UV absorbers are 2-hydroxy-4-methoxybenzophenone, salicylic acid phenyl ester or 3-(2'-hydroxy-5'-methylphenyl)-benzotriazole.

Since the teeth are to be restored as close to nature as possible, it is necessary to provide the tooth filling materials or dental varnishes for a wide range of different tooth shades. Inorganic colourings and organic pigments in very small quantities are generally used for this purpose. Such colourings or pigments are also other constituents which may be present as or in component (g) in tooth filling materials or dental varnishes according to the invention.

In addition to the other constituents set out above, the person skilled in the art knows of other constituents which are used in conventional tooth filling materials or dental varnishes. Other constituents are often added in small quantities as additives in order, for example, to improve the mechanical or optical properties of tooth filling materials or dental varnishes or of hardened tooth filling materials or dental varnishes.

According to the invention, tooth filling materials or dental varnishes are preferred comprising (e) one or more additives selected from the group comprising silver, substances releasing silver ions, copper, substances releasing copper ions, zinc and substances releasing zinc ions, and/or (f) one, two, three or more softeners, preferably polyethylene glycol as the softener, and/or (g) one or more other constituents.

Constituents which can be associated technically and in terms of terminology with two or more components are particularly associated with the earlier mentioned component for the purposes of quantitative data for the avoidance of misunderstandings (therefore, (a) before (b) before (c) before (d) before (e) before (f) before (g)).

The person skilled in the art will select for tooth filling materials or dental varnishes according to the invention the proportion of the one or more compounds of the formula (I) so that the effect desired by him in relation to inhibiting the biofilm formation of *Streptococcus mutans* is achieved, with the person skilled in the art preferably taking care, on the one hand, not to use excessively large total quantities of the one or more compounds of the formula (I) and, on the other hand, not merely to provide such a small quantity of the one or more compounds of the formula (I) that inhibition of the biofilm formation of *Streptococcus mutans* cannot be perceived or cannot be perceived to a significant degree.

Tooth filling materials or dental varnishes are preferred according to the invention comprising as the active substance for inhibiting the biofilm formation of *Streptococcus mutans* a total of from 0.001 µg/ml to 2500 µg/ml, preferably from 0.01 µg/ml to 250 µg/ml, particularly preferably from 0.1 µg/ml to 25 µg/ml of the one (if only one compound of the formula (I) is present) or all the compounds of the formula (I) (if a plurality are present), in relation to the volume of the tooth filling material or dental varnish.

In a particularly preferred embodiment, tooth filling materials or dental varnishes according to the invention are characterised in that the compound of the formula (I) is contained in such a quantity in the tooth filling material or dental varnish that the biofilm inhibition on (a) the tooth filling materials or dental varnishes and/or on (b) the tooth filling materials or dental varnishes hardened by hardening is at least 10%, preferably at least 30%, particularly preferably at least 50%.

Particularly preferred tooth filling materials according to the invention comprise as component (a)

a total of from 0.001 µg/ml to 2500 µg/ml, preferably from 0.01 µg/ml to 250 µg/ml, particularly preferably from 0.1 µg/ml to 25 µg/ml, of the compounds of the formula (I), in relation to the volume of the tooth filling material, as component (b)

a total of from 5% by weight to 50% by weight, preferably from 10% by weight to 35% by weight, particularly preferably from 15% by weight to 25% by weight of the material for forming a structure for the uptake and delayed release of the active substance comprising one, two, three or more polymerisable monomers, in relation to the total weight of the tooth filling material, as component (c)

a total of from 40% by weight to 90% by weight, preferably from 55% by weight to 85% by weight, particularly preferably from 70% by weight to 80% by weight of the inorganic filling material or the filling material admixture, in relation to the total weight of the tooth filling material, as component (d)

a total of from 0.001% by weight to 10% by weight, preferably from 0.01% by weight to 5% by weight, particularly preferably from 0.01% by weight to 2% by weight of the initiators, accelerators and/or inhibitors, in relation to the total weight of the tooth filling material, as component (f)

a total of from 0% by weight to 25% by weight, preferably from 0.01% by weight to 15% by weight, particularly preferably from 0.1% by weight to 5% by weight of a softener, in relation to the total weight of the tooth filling material, and as component (g)

a total of from 0% by weight to 15% by weight of additional constituents in relation to the total weight of the tooth filling material.

Particularly preferred dental varnishes according to the invention comprise as component (a)
a total of from 0.001 μg/ml to 2500 μg/ml, preferably from 0.01 μg/ml to 250 μg/ml, particularly preferably from 0.1 μg/ml to 25 μg/ml of the compounds of the formula (I), in relation to the volume of the dental varnish, as component (b)
a total of from 40% by weight to 99% by weight, preferably from 50% by weight to 97% by weight, particularly preferably from 60% by weight to 95% by weight of the material for forming a structure for the uptake and delayed release of the active substance comprising one, two, three or more polymerisable monomers, in relation to the total weight of the dental varnish, as component (c)
a total of from 0.1% by weight to 10% by weight, preferably from 0.5% by weight to 8% by weight, particularly preferably from 1% by weight to 5% by weight of the inorganic filling material or the filling material admixture, in relation to the total weight of the dental varnish, as component (d)
a total of from 0.001% by weight to 10% by weight, preferably from 0.01% by weight to 5% by weight, particularly preferably from 0.01% by weight to 2% by weight of the initiators, accelerators and/or inhibitors, in relation to the total weight of the dental varnish, as component (f)
a total of from 0% by weight to 15% by weight, preferably from 0.01% by weight to 10% by weight, particularly preferably from 0.1% by weight to 5% by weight of the softener, in relation to the total weight of the dental varnish, and as component (g)
a total of from 0% by weight to 15% by weight of additional constituents in relation to the total weight of the tooth filling material.

So that the best possible mechanical properties (for example, flexural strength or abrasion resistance) of the hardened tooth filling materials or dental varnishes according to the invention and, at the same time, a good uptake and delayed release of the active substance can take place, it has been found in our own research that it is advantageous to mix together the individual components very well so that the result is an admixture which comprises a homogeneous phase, in which filler particles are present in a manner distributed uniformly (homogeneously). The homogeneous phase consequently forms the continuous phase of a dispersion. Accordingly, there are particularly preferred according to the invention tooth filling materials or dental varnishes where the component (a) forms a homogeneous phase with the component (b) and/or where the component (c) is uniformly suspended in the admixture of (a) and (b).

Tooth filling materials or dental varnishes are preferred according to the invention for use in a method for the therapeutic (including prophylactic) treatment of the human or animal body,
preferably for use
in a method for inhibiting, reducing or preventing tooth damage, in particular tooth damage which is caused by *Streptococcus mutans*,
and/or
in a method for inhibiting, reducing or preventing dental caries.

Tooth filling materials or dental varnishes are particularly preferred according to the invention for use in a therapeutic method for inhibiting, reducing or preventing biofilms, preferably bacterial biofilms.

In a preferred embodiment, the invention relates to tooth filling materials for inhibiting the biofilm formation of *Streptococcus mutans*, preferably for use in a method for the therapeutic (including prophylactic) treatment of the human or animal body, comprising:

(a) as the active substance for inhibiting the biofilm formation of *Streptococcus mutans* a total of from 0.1 μg/ml to 25 μg/ml of a compound of the formula (II) in relation to the total weight of the tooth filling material, (b) a total of from 15% by weight to 25% by weight of a material for forming a structure for the uptake and delayed release of the active substance comprising one, two, three or more polymerisable monomers, in relation to the total weight of the tooth filling material,
where the one polymerisable monomer or one, two, three, a plurality of or all of the plurality of polymerisable monomers is/are selected from the group of (meth)acrylates, is/are preferably selected from the group comprising triethylene glycol dimethacrylate (TEGDMA), urethane dimethacrylate (7,7,9-trimethyl-4,13-dioxo-3,14-dioxa-5,12-diazahexadecan-1,16-dioxydimethacrylate (UDMA)), glycerol dimethacrylate (GlyDMA), bisphenol-A-glycidyl-methacrylate (Bis-GMA), 1,12-dodecandiol dimethacrylate (DODMA), hydroxyethyl methacrylate (HEMA), polyethylene glycol dimethacrylate (PEGDMA) and ethoxylated bisphenol-A-dimethacrylate (EtoBG), (c) a total of from 70% by weight to 80% by weight of one or more inorganic particulate filling materials, where the one or one or more or all of the inorganic filling materials are selected from the group comprising silanised dental glass particles and pyrogenic and/or non-agglomerated and/or non-aggregated silicic acids, in relation to the total weight of the tooth filling material,
and (d) a total of from 0.01% by weight to 2% by weight of one or more additives selected from the group comprising initiators, accelerators and inhibitors, in relation to the total weight of the tooth filling material,
and optionally (e) one or more additives selected from the group comprising silver, substances releasing silver ions, copper, substances releasing copper ions, zinc and substances releasing zinc ions,
and optionally (f) polyethylene glycol as the softener
and optionally (g) one or more other constituents.

In a preferred embodiment, the invention relates to dental varnishes for inhibiting the biofilm formation of *Streptococcus mutans*, preferably for use in a method for the therapeutic (including prophylactic) treatment of the human or animal body, comprising:

(a) as the active substance for inhibiting the biofilm formation of *Streptococcus mutans*, a total of from 0.1 μg/ml to 25 μg/ml of a compound of the formula (II), in relation to the total weight of the dental varnish, (b) a total of from 60% by weight to 90% by weight of a material for forming a structure for the uptake and delayed release of the active substance comprising one, two, three or more polymerisable monomers, in relation to the total weight of the dental varnish,
where the one polymerisable monomer or one, two, three, a plurality of or all of the plurality of polymerisable monomers is/are selected from the group of (meth)acrylates, is/are preferably selected from the group comprising triethylene glycol dimethacrylate (TEGDMA), urethane dimethacrylate (7,7,9-trimethyl-4,13-dioxo-3,14-dioxa-5,12-diazahexadecan-1,16-dioxydimethacrylate (UDMA)), glycerol dimethacrylate (GlyDMA), bisphenol-A-glycidyl-methacrylate (Bis-GMA), 1,12-dodecandiol dimethacrylate (DODMA), hydroxyethyl methacrylate (HEMA), polyethylene glycol dimethacrylate (PEGDMA) and ethoxylated bisphenol-A-dimethacrylate (EtoBG), (c) a total of from 1% by weight to 5% by weight of one or more inorganic particulate fillers, where the one or one or more or all of the inorganic filling materials are selected from the group comprising pyrogenic and/or non-agglomerated and/or non-aggregated silicic acids, in relation to the total weight of the dental varnish, and (d) a total of from 0.01% by weight to 2% by weight of one or more additives selected from the group comprising initiators, accelerators and inhibitors, in relation to the total weight of the dental varnish, and optionally (e) one or more additives selected from the group comprising silver, substances releasing silver ions, copper, substances releasing copper ions, zinc and substances releasing zinc ions, and optionally (f) polyethylene glycol as the softener and optionally (g) one or more other constituents.

The invention further relates to a method for producing tooth filling materials or dental varnishes according to the invention having the following steps:

(i) providing or producing (a) a quantity of one or more compounds of the formula (I) (as defined above, preferably as referred to above as being preferable) as the active substance for inhibiting the biofilm formation of *Streptococcus mutans*, preferably as an alcoholic solution, (ii) providing or producing (b) a material for forming a structure for the uptake and delayed release of the active substance comprising one, two, three or more polymerisable monomers, (iii) providing or producing (c) one or more particulate fillers, (iv) providing or producing (d) one or more additives selected from the group comprising initiators, accelerators and inhibitors, (v) optionally providing or producing (e) one or more additives selected from the group comprising silver, substances releasing silver ions, copper, substances releasing copper ions, zinc and substances releasing zinc ions, (f) one, two, three or more softeners, preferably polyethylene glycol as the softener and/or (g) one or more other constituents and (vi) mixing the components provided and/or produced.

The invention also relates to a kit comprising:

a tooth filling material according to the invention or dental varnish according to the invention (as defined above, preferably as referred to above as being preferable) and one or more additional constituents selected from the group comprising adhesives, abutments, implants, forming tools, impression materials, colour scales, colour guides and light hardening devices.

Another aspect of the present invention is the use of a compound of the formula (I) (as defined above, preferably as referred to above as being preferable) for producing a tooth filling material or dental varnish according to the invention.

The invention also relates to a (therapeutic, in particular prophylactic, or cosmetic) method for inhibiting the biofilm formation of *Streptococcus mutans*, in the oral cavity of a patient having the following steps:

providing or producing a tooth filling material or dental varnish according to the invention (as defined above, preferably as referred to above as being preferable), applying the provided or produced tooth filling material or dental varnish to a surface in the oral cavity of a patient, preferably to a tooth surface in the oral cavity of a patient, optionally forming the applied tooth filling material or dental varnish on the surface in the oral cavity of the patient, hardening, or allowing to harden of the applied tooth filling material or dental varnish, which is optionally formed, on the surface in the oral cavity of the patient and optionally further post-treating the hardened tooth filling material or dental varnish on the surface in the oral cavity of the patient, preferably by polishing and/or grinding.

The invention also relates to a (first) method for producing a dental prosthesis which inhibits the biofilm formation having the following steps:

providing a dental prosthesis, providing or producing a tooth filling material or dental varnish (as defined above, preferably as referred to above as being preferable), applying the provided or produced tooth filling material or dental varnish to the dental prosthesis, optionally forming the applied tooth filling material or dental varnish on the dental prosthesis, optionally hardening, or allowing to harden of the applied tooth filling material or dental varnish, which is optionally formed, on the dental prosthesis and optionally further post-treating the hardened tooth filling material or dental varnish on the dental prosthesis, preferably by polishing and/or grinding.

As an alternative to the first method for producing a dental prosthesis which inhibits the biofilm formation, the invention also relates to a (second) method for producing a dental prosthesis which inhibits the biofilm formation having the following steps:

providing or producing a tooth filling material or dental varnish according to the invention (as defined above, preferably as referred to above as being preferable), forming the tooth filling material or dental varnish, hardening, or allowing to harden of the formed tooth filling material or dental varnish and optionally further post-treating the hardened tooth filling material or dental varnish.

Both methods for producing a dental prosthesis which inhibits the biofilm formation can preferably be configured as a so-called chair-side method. However, it will be understood that, although the methods according to the invention may be configured as chair-side methods, they do not have to be configured as chair-side methods. In a large number of cases, it is advantageous to select a method configuration, in place of a chair-side method, in which no individual method step takes place in the mouth of or on the patient. Such method configurations are also referred to as lab-side methods.

Other aspects of the present invention will arise from the following experimental methods, examples and patent claims.

PRODUCTION EXAMPLE

Production of Silicic Acid Particles Surface-Modified by Means of Organic Structural Elements General Provision A colloidal dispersion of wet-chemically produced, inorganic filler particles of suitable mean particle size is provided, with an organic, water-soluble matrix, for example, isopropanol, being used as the dispersion medium.

The dispersion is mixed with
(a) a sufficient quantity of a surface modification agent which has, on the one hand, alkoxysilane groups and, on the other hand, organic groups which can be converted with radically polymerisable monomers so as to form covalent bonds (such a surface modification agent is, for example, 3-methacryloyloxy propyl trialkoxysilane),
(b) a two-fold to ten-fold molar quantity of water in relation to the surface modification agent and
(c) approximately 1% by weight in relation to the surface modification agent of methacrylic acid.

The resultant admixture is stirred for at least 8 hours at from 50 to 80° C. so that the surface modification of the inorganic filling material particles used can be carried out completely.

Production of Silanised $SiO_2$ Nanoparticles

The silanised $SiO_2$ nanoparticles are produced according to the general provision for producing surface-modified silicic acid particles by means of organic structural elements, where the following materials are used. Those silanised $SiO_2$ nanoparticles are used in examples 1, 2, 3, 4 and 7.

Materials for producing silanised $SiO_2$ nanoparticles:

| | |
|---|---|
| 864 g | of a 20% suspension in ethanol of non-flame-hydrolytically produced silicic acid particles (having a mean particle size of 40 nm), |
| 40 g | of gamma-methacryloyloxy propyl silane (23% in relation to the solid material proportion, for surface modification), |
| 0.4 g | of methacrylic acid and |
| 18 g | of water. |

Example 1

Producing a Tooth Filling Material According to the Invention

The following components were weighed in a glass beaker, with the weight values in percent relating to the total quantity of the completed admixture:

| | | |
|---|---|---|
| ethoxylated bisphenol-A-dimethacrylate (EtoBG) | 10.00% | by weight Component b) |
| triethylene glycol dimethacrylate (TEGDMA) | 9.9975% | by weight Component b) |
| 1,6-hexanediol dimethacrylate (HEDMA) | 4.75% | by weight Component b) |
| camphor quinone | 0.10% | by weight Component d) |
| ethyl-p-N,N-dimethylamino benzoate (DABE) | 0.15% | by weight Component d) |
| carolacton | 0.0025% | by weight Component a) |

Subsequently, the admixture was homogenised with a KPG stirrer for 12 hours. The following fillers:

| | | |
|---|---|---|
| $SiO_2$ nanoparticles, silanised | 25.00% | by weight Component c) |
| Dental glass 3.5 μm | 50.00% | by weight Component c) | were added to this admixture and a homogeneous paste was produced by intimate mixing with a double planetary mixer and subsequently vented under vacuum.

Example 2

Producing a Tooth Filling Material According to the Invention

The following components were weighed in a glass beaker, with the weight values in percent relating to the total quantity of the completed admixture:

| | | |
|---|---|---|
| ethoxylated bisphenol-A-dimethacrylate (EtoBG) | 8.00% | by weight Component b) |
| triethylene glycol dimethacrylate (TEGDMA) | 7.998% | by weight Component b) |
| 1,6-hexanediol dimethacrylate (HEDMA) | 3.8% | by weight Component b) |
| camphor quinone | 0.08% | by weight Component d) |
| ethyl-p-N,N-dimethylamino benzoate (DABE) | 0.12% | by weight Component d) |
| carolacton | 0.002% | by weight Component a) |

Subsequently, the admixture was homogenised with a KPG stirrer for 12 hours. The following fillers:

| | | |
|---|---|---|
| $SiO_2$ nanoparticles, silanised | 9.00% | by weight Component c) |
| Dental glass, silanised d50 = 3.5 μm | 58.00% | by weight Component c) |
| Dental glass, silanised d50 = 1.0 μm | 13.00% | by weight Component c) | were added to this admixture and a homogeneous paste was produced by intimate mixing with a double planetary mixer and subsequently vented under vacuum.

Example 3

Producing a Tooth Filling Material According to the Invention

The following components were weighed in a glass beaker, with the weight values in percent relating to the total quantity of the completed admixture:

| | | |
|---|---|---|
| ethoxylated bisphenol-A-dimethacrylate (EtoBG) | 8.80% | by weight Component b) |
| triethylene glycol dimethacrylate (TEGDMA) | 8.7978% | by weight Component b) |
| 1,6-hexanediol dimethacrylate (HEDMA) | 4.12% | by weight Component b) |
| camphor quinone | 0.088% | by weight Component d) |
| ethyl-p-N,N-dimethylamino benzoate (DABE) | 0.132% | by weight Component d) |
| carolacton | 0.0022% | by weight Component a) |

Subsequently, the admixture was homogenised with a KPG stirrer for 12 hours. The following fillers:

| | |
|---|---|
| SiO₂ nanoparticles, silanised | 10.80% by weight Component c) |
| Dental glass, silanised d50 = 3.5 μm | 53.40% by weight Component c) |
| Dental glass, silanised d50 = 1.0 μm | 13.80% by weight Component c) | were added to this admixture and a homogeneous paste was produced by intimate mixing with a double planetary mixer and subsequently vented under vacuum.

Example 4

Producing a Tooth Filling Material According to the Invention

The following components were weighed in a glass beaker, with the weight values in percent relating to the total quantity of the completed admixture:

| | |
|---|---|
| bisphenol-A-glycidyl-methacrylate (Bis-GMA) | 7.04% by weight Component b) |
| triethylene glycol dimethacrylate (TEGDMA) | 7.81% by weight Component b) |
| (7,7,9-trimethyl-4,13-dioxo-3,14-dioxa-5,12-diazahexadecan-1,16-dioxydimethacrylate (UDMA) | 7.04% by weight |
| camphor quinone | 0.044% by weight Component d) |
| ethyl-p-N,N-dimethylamino benzoate (DABE) | 0.066% by weight Component d) |
| carolacton | 0.0025% by weight Component a) |

Subsequently, the admixture was homogenised with a KPG stirrer for 12 hours. The following fillers:

| | |
|---|---|
| SiO₂ nanoparticles, silanised | 10.80% by weight Component c) |
| Dental glass, silanised d50 = 3.5 μm | 53.3975% by weight Component c) |
| Dental glass, silanised d50 = 1.0 μm | 13.80% by weight Component c) | were added to this admixture and a homogeneous paste was produced by intimate mixing with a double planetary mixer and subsequently vented under vacuum.

Example 5

Producing a Dental Varnish According to the Invention

The following components were weighed in a glass beaker, with the weight values in percent relating to the total quantity of the completed admixture:

| | |
|---|---|
| trimellitic acid anhydride-4-methacryloyl oxyethyl ester (4-META) | 14.9975% by weight Component b) |
| 1,6-hexanediol dimethacrylate (HEDMA) | 7.5% by weight Component b) |
| (7,7,9-trimethyl-4,13-dioxo-3,14-dioxa-5,12-diazahexadecan-1,16-dioxydimethacrylate (UDMA) | 47% by weight |
| triethylene glycol dimethacrylate (TEGDMA) | 10% by weight Component b) |
| 1,12-dodecandiol dimethacrylate (DODMA) | 7.5% by weight Component b) |
| bisphenol-A-glycidyl-methacrylate (Bis-GMA) | 6% by weight Component b) |
| PEG 300 | 3.5% by weight Component f) |
| camphor quinone | 0.81% by weight Component d) |
| ethyl-p-N,N-dimethylamino benzoate (DABE) | 1.215% by weight Component d) |
| carolacton | 0.0025% by weight Component a) |

Subsequently, the admixture was homogenised with a KPG stirrer for 12 hours. The following fillers:

| | |
|---|---|
| Aerosil R972 | 1.5% by weight Component c) | were added to this admixture and a homogeneous paste was produced by intimate mixing with a double planetary mixer and subsequently vented under vacuum.

Example 6

Producing a Dental Varnish According to the Invention

The following components were weighed in a glass beaker, with the weight values in percent relating to the total quantity of the completed admixture:

| | |
|---|---|
| 1,6-hexanediol dimethacrylate (HEDMA) | 12.5% by weight Component b) |
| (7,7,9-trimethyl-4,13-dioxo-3,14-dioxa-5,12-diazahexadecan-1,16-dioxydimethacrylate (UDMA) | 31% by weight |
| triethylene glycol dimethacrylate (TEGDMA) | 19.9975% by weight Component b) |
| 1,12-dodecandiol dimethacrylate (DODMA) | 7.5% by weight Component b) |
| ethoxylated bisphenol-A-dimethacrylate (EtoBG) | 16% by weight |
| bisphenol-A-glycidyl-methacrylate (Bis-GMA) | 6% by weight Component b) |
| PEG 300 | 3.5% by weight Component f) |
| camphor quinone | 0.81% by weight Component d) |
| ethyl-p-N,N-dimethylamino benzoate (DABE) | 1.215% by weight Component d) |
| carolacton | 0.0025% by weight Component a) |

Subsequently, the admixture was homogenised with a KPG stirrer for 12 hours. The following filler

| | |
|---|---|
| Aerosil R972 | 1.5% by weight Component c) | were added to this admixture and a homogeneous paste was produced by intimate mixing with a double planetary mixer and subsequently vented under vacuum.

Example 7

Producing a Tooth Filling Material According to the Invention

Example 7a

Producing the Catalyst Admixture

For producing the catalyst admixture, the following components were weighed in a glass beaker, with the weight values in percent relating to the total quantity of the completed catalyst admixture:

| | | |
|---|---|---|
| (7,7,9-trimethyl-4,13-dioxo-3,14-dioxa-5,12-diazahexadecan-1,16-dioxydimethacrylate (UDMA) | 12% by weight | Component a) |
| polyethylene glycol dimethacrylate | 12.3475% by weight | Component a) |
| stabiliser | 0.15% by weight | Component b) |
| benzoyl peroxide | 0.5% by weight | Component b) |
| carolacton | 0.0025% by weight | Component a) |

Subsequently, the admixture was homogenised with a KPG stirrer for 12 hours. The following fillers:

| | |
|---|---|
| SiO$_2$ nanoparticles, silanised | 25.00% by weight Component c) |
| Dental glass, 3.5 µm | 50.00% by weight Component c) | were added to this admixture and a homogeneous paste was produced by intimate mixing with a double planetary mixer and subsequently vented under vacuum.

Example 7b

Producing the Base Admixture

For producing the base admixture, the following components were weighed in a glass beaker, with the weight values in percent relating to the total quantity of the completed catalyst admixture:

| | | |
|---|---|---|
| (7,7,9-trimethyl-4,13-dioxo-3,14-dioxa-5,12-diazahexadecan-1,16-dioxydimethacrylate (UDMA) | 12.1975% by weight | Component a) |
| polyethylene glycol dimethacrylate | 12.00% by weight | Component a) |
| N,N-bis(dihydroxyethyl-p-toluidine | 0.5% by weight | Component b) |
| camphor quinone | 0.15% by weight | Component b) |
| coinitiator | 0.15% by weight | Component b) |
| carolacton | 0.0025% by weight | Component a) |

The admixture was homogenised with a KPG stirrer for 12 hours. The following fillers:

| | |
|---|---|
| SiO$_2$ nanoparticles, silanised | 25.00% by weight Component c) |
| Dental glass 3.5 µm | 50.00% by weight Component c) | were added to this admixture and a homogeneous paste was produced by intimate mixing with a double planetary mixer and subsequently vented under vacuum.

Example 8

Comparison of the Colony-Forming Units of *Streptococcus mutans* (CFU) after Treatment with Carolacton, Chlorohexidine and Triclosan In a THB nutrition medium, an over-night culture of *Streptococcus mutans* UA159 was cultivated anaerobically. That over-night culture was diluted to an optimum density (at 620 nm; OD$_{620}$) of from 0.01 to 0.03 with THB (with addition of 0.5% (GN) of saccharose) so that a dilute bacterial suspension was obtained.

Stock solutions and corresponding diluted solutions of chlorohexidine, triclosan and carolacton were produced in methanol. 10 nl of those solutions to be tested were introduced by pipette into microtitration plates; 9 parallel wells were used per substance and concentration. The methanol was evaporated (under a hood) and then 200 µl of the dilute bacterial suspension were added. The final concentrations of the active substances in the 200 µl of bacterial suspension were 0.25 µg/ml and 2.5 µg/ml. The plates were incubated anaerobically at 37° C. without agitation for 20 hours. Subsequently, the excess was removed by pipette, the biofilm was washed with a physiological cooking salt solution (0.85% of NaCl) and the biofilm was scraped off with a pipette. The biofilms from three parallel wells were suspended in 500 µl of PBS. From that biofilm suspension, a serial dilution in PBS was prepared. After each dilution step, vortexing was carried out for 1 minute. From each dilution, 50 µl was distributed three times on agar plates (TH medium). The plates were incubated for three days in the CO$_2$ cupboard at 37° C., then the colony-forming units (CFU) were counted and the bacteria density in relation to 1000 ml of biofilm suspension was calculated.

The results obtained clearly show in comparison that triclosan and chlorohexidine at both final concentrations mentioned result in a very powerful reduction in the colony-forming units, whereas carolacton merely weakly reduces the number of colony-forming units. Consequently, triclosan and chlorohexidine have a great antimicrobial action in solution whereas the antimicrobial action of carolacton is only weak.

Example 9

Comparative Determination of the Biofilm Inhibition with Use of Tooth Filling Materials Preparation of the Microtitration Plate:

The admixture from example 2 was used as the tooth filling material according to the invention.

In addition, three tooth filling materials similar to example 2 were prepared, where carolacton was replaced with triclosan in a first comparison admixture, carolacton was replaced with chlorohexidine in a second comparison admixture and carolacton was omitted in a third comparison admixture (control).

From each of the tooth filling materials produced, by hardening the tooth filling material 10 dental test members were produced with a diameter of 7 mm and a height of 1 mm and adhesively bonded with a small quantity of the tooth filling material in a total of 40 wells of a 96-well microtitration plate of polystyrene (Greiner Bio-One, µ Clear Plate Black, Frickenhausen, Germany).

Cultivation of the Biofilm

In a THB nutrition medium, an over-night culture of *Streptococcus mutans* UA159 was produced under anaerobic conditions. The over-night culture obtained was diluted to an optimum density (at 620 nm; OD$_{620}$) of from 0.01 to 0.03 with THB (with addition of 0.5% (G/V) of saccharose). Subsequently, 200 µl of the dilute over-night culture was introduced by pipette into the wells of the 96-well microtitration plate provided with the dental test members. The microtitration plate was subsequently incubated for 20 hours at 37° C. under anaerobic conditions in an incubator.

Determination of the Biofilm Inhibition

The determination of the biofilm inhibition was carried out with a LIVE/DEAD BacLight kit L13152 (Invitrogen, Molecular Probes, Inc. Eugene, Oreg., USA), taking note of the manufacturer's instructions. The kit comprises two dye solutions, propidium iodide and SYTO9 which each discolour nucleic acids. The excesses of the biofilms in the individual wells of the 96-well microtitration plate were removed. In order to remove plankton-like or loosely bonded bacteria, the biofilm was carefully washed with 200 μl of a 0.85% NaCl solution, mixed with 200 μl of a 1:1 admixture of propidium iodide and SYTO9 and subsequently left to stand for 15 minutes and at ambient temperature with light being excluded. The measurement of the fluorescence was carried out on a Wallac Victor3™ 1420Multilabel Counter (Perkin-Elmer Life Sciences) provided with detectors and filters for measuring the fluorescence at 630 nm (red) and 535 nm (green). The biofilm inhibition is given in percent as a quotient between the quotient of green and red fluorescence of the sample with the active substance (carolacton, chlorohexidine or triclosan) and the quotient of green and red fluorescence of the sample without any active substance (control). The results are set out in the following Table 1:

TABLE 1

| Active substance | Biofilm inhibition [%] |
|---|---|
| Carolacton (25 μg/ml) | 51 |
| Triclosan (2500 μg/ml) | 1 |
| Chlorohexidine (2500 μg/ml) | 1 |

The results clearly show that carolacton brings about a very good biofilm inhibition whereas triclosan and chlorohexidine scarcely influence the biofilm formation.

Determination of Colony-Forming Units in the Biofilm:

The results for the determination of colony-forming units in the biofilm (procedure for the determination as in Example 8) surprisingly demonstrate a powerful inhibiting effect of carolacton on the biofilm whereas neither triclosan nor chlorohexidine, although used at a hundred times the concentration of carolacton, results in a powerful reduction of the number of CFU.

TABLE 2

| | Mean value [cfu/mL] | Standard error [cfu/mL] | Remaining CFU % (scaling to control) | Inhibition % |
|---|---|---|---|---|
| tooth filling material with triclosan 2500 μg/ml | 6,593,333 | 1,311,111 | 89 | 11 |
| tooth filling material with chlorohexidine 2500 μg/ml | 4,220,000 | 786,667 | 57 | 43 |
| tooth filling material with carolacton 25 μg/ml | 113,333 | 22,222 | 2 | 98 |
| tooth filling material without active substance (control) | 7,426,667 | 2,111,111 | 100 (= standardised) | 0 |

Example 10

Determining the Flexural Strength of the Hardened Tooth Filling Material According to the Invention The determination of the flexural strength is carried out similarly to ISO4049. To that end, a test member having dimensions of 2×2 mm is measured. Hardening is carried out for 20 seconds at a suitable wavelength for light-hardening compositions.

In order to determine the flexural strength after temperature cycles ("flexural resistance TC"), the test member is subjected to 3000 temperature cycles between 5 and 55° C. (for this purpose, it is laid alternately for one minute in a bath at a temperature of 55° C. and subsequently for one minute in a bath at a temperature of 5° C.) and subsequently measured.

The determination of the flexural strength was carried out for the tooth filling materials from examples 2, 3 and 4. The results are set out in the following Table 3.

TABLE 3

| | Example 2 | Example 3 | Example 4 |
|---|---|---|---|
| Flexural strength (24 h) [MPa] | 141 | 152 | 121 |
| Flexural strength TC [MPa] | 122 | 127 | 106 |

Example 11

Determining the Water Absorption

The water absorption was determined analogously to ISO 4049. To that end, the tooth filling materials were introduced into corresponding Teflon moulds without air bubbles, covered with foils and glass plates and the excesses were pressed out with a screw type clamp. The specimen having a diameter of 15.0±0.1 mm and a height of 1.0±0.1 mm were light-hardened in segments. Subsequently, the specimen were stored in a desiccator at 37° C. After 22 hours, the specimen were removed, brought to 23° C. for two hours in a second desiccator and then weighed to within 0.1 mg. That cycle was repeated until a constant mass $m_1$ was achieved.

After complete drying, the diameter was measured twice at right angles to each other with a measurement accuracy of 0.01 mm and the mean diameter was calculated therefrom. The thickness of the test member was measured at the centre and at four locations of the edge with identical spacing to within 0.01 mm. The volume V was calculated from the mean diameter and the mean thickness.

Subsequently, the specimen were stored for 7 days in water at 37° C. Subsequently, the specimen were taken out, flushed with water and dabbed until no further moisture was visible on the surface. The specimen were pivoted back and forth in the air for 15 seconds and weighed 1 minute after being taken out of the water. That mass is set out as $m_2$.

Subsequently, the specimen were again stored in a desiccator at 37° C. After 22 hours, the specimen were removed, brought to 23° C. for two hours in a second desiccator and then weighed to within 0.1 mg. That cycle was repeated until a constant mass $m_3$ was achieved.

The water absorption $W_{sp}$ was calculated according to the following equation:

$$W_{sp} = \frac{m_2 - m_3}{V}$$

Where:
$m_2$ is the mass of the specimen after water storage for 7 days in μg;
$m_3$ is the mass of the specimen dried again in μg;
V is the volume of the specimen in $mm^3$.

The determination of the water absorption was carried out for the tooth filling materials from examples 2, 3 and 4. The results are set out in the following Table 4.

TABLE 4

| | Example 2 | Example 3 | Example 4 |
|---|---|---|---|
| Water absorption [μg/mm³] | 10 | 12 | 15.5 |

The invention claimed is:

1. Tooth filling materials or dental varnishes for inhibiting the formation of biofilms of *Streptococcus mutans* comprising:
   (a) 0.001 μg/ml to 2500 μg/ml of carolacton of formula (II) as the active substance for inhibiting the formation of biofilms of *Streptococcus mutans* and
   (b) a material for forming a structure for the uptake and delayed release of the active substance comprising one, two, three or more polymerisable or polymerized monomers,
   and
   (c) one or more particulate fillers,
   and
   (d) one or more additives selected from the group comprising initiators, accelerators and inhibitors, wherein concentrations are expressed in relation to the volume of the tooth filling material or dental varnish.

2. Tooth filling material or dental varnish according to claim 1, wherein the one polymerisable monomer or one, two, three, a plurality of or all the plurality of polymerisable or polymerized monomers of the component (b) is/are selected from the group of (meth)acrylates and (meth)acrylamides.

3. Tooth filling material or dental varnish according to claim 1, comprising as the active substance for inhibiting the biofilm formation of *Streptococcus mutans* a total of from 0.01 μg/ml to 250 μg/ml of the compound of formula (II), in relation to the volume of the tooth filling material or dental varnish.

4. Tooth filling material or dental varnish according to claim 1, comprising in or as component
   (c) one or more inorganic particulate fillers, the one or one or more or all of the inorganic particulate filling materials being selected from the group consisting of silanised $SiO_2$ nanoparticles, pyrogenic and/or non-agglomerated and/or non-aggregated silicic acids, non-aggregated, non-agglomerated $SiO_2$ nanoparticles, dental glass particles, silanised dental glass particles, zirconium oxide particles, aluminium oxide particles and inorganic filling material particles surface-modified by means of organic structural elements.

5. Tooth filling material or dental varnish according to claim 1 comprising
   (e) one or more additives selected from the group consisting of silver, substances releasing silver ions, copper, substances releasing copper ions, zinc and substances releasing zinc ions,
   and/or
   (f) one, two, three or more softeners,
   and/or
   (g) other constituents.

6. A method for the therapeutic treatment of a human or animal body, comprising:
   providing a tooth filling material or dental varnish according to claim 1, and
   applying the tooth filling material or dental varnish to a tooth, wherein application of the tooth filling material or dental varnish inhibits, reduces or prevents (1) tooth damage caused by *Streptococcus mutans*, and/or (2) dental caries.

7. A method for the therapeutic treatment of a human or animal body, comprising:
   providing a tooth filling material or dental varnish according to claim 1, and
   applying the tooth filling material or dental varnish to a tooth, wherein application of the tooth filling material or dental varnish inhibits, reduces or prevents biofilms on or adjacent the tooth filling material or dental varnish.

8. Method for producing a tooth filling material or dental varnish as defined in claim 1, having the following steps:
   (i) providing or producing (a) a quantity of carolacton of formula (II) as the active substance for inhibiting the biofilm formation of *Streptococcus mutans*,
   (ii) providing or producing (b) a material for forming a structure for the uptake and delayed release of the active substance comprising one, two, three or more polymerisable monomers,
   (iii) providing or producing (c) one or more particulate fillers,
   (iv) providing or producing (d) one or more additives selected from the group comprising initiators, accelerators and inhibitors,
   (v) optionally providing or producing
      (e) one or more additives selected from the group comprising silver, substances releasing silver ions, copper, substances releasing copper ions, zinc and substances releasing zinc ions,
      (f) one, two, three or more softeners,
      and/or
      (g) one or more other constituents
   and
   (vi) mixing the components provided and/or produced, wherein the carolacton of formula (II) is present in the resulting tooth filling material or dental varnish at a concentration of 0.001 μg/ml to 2500 μg/ml.

9. Kit comprising:
   a tooth filling material or dental varnish according to claim 1 and
   one or more additional constituents selected from the group comprising adhesives, abutments, implants, forming tools, impression materials, colour scales, colour guides and light hardening devices.

10. A method for producing a tooth filling material or dental varnish, comprising:
   providing a tooth filing material or dental varnish according to claim 1, and
   applying the tooth filling material or dental varnish to a tooth.

11. Method for producing a dental prosthesis which inhibits the biofilm formation having the following steps:
provide a dental prosthesis,
providing or producing a tooth filling material or dental varnish as defined in claim 1,
applying the provided or produced tooth filling material or dental varnish to the dental prosthesis,
optionally forming the applied tooth filling material or dental varnish on the dental prosthesis,
optionally hardening, or allowing to harden of the applied tooth filling material or dental varnish, which is optionally formed, on the dental prosthesis and
optionally further post-treating the hardened tooth filling material or dental varnish on the dental prosthesis, preferably by polishing and/or grinding.

12. Method for producing a dental component which inhibits the biofilm formation having the following steps:
providing or producing a tooth filling material or dental varnish as defined in claim 1,
forming the tooth filling material or dental varnish,
hardening, or allowing to harden of the formed tooth filling material or dental varnish and
optionally further post-treating the hardened formed tooth filling material or dental varnish.

13. The method according to claim 8, wherein component (i) comprises a quantity of the compound of the formula (II) as an alcoholic solution.

14. Tooth filling material or dental varnish according to claim 1, comprising as the active substance for inhibiting the biofilm formation of *Streptococcus mutans* a total of from 0.1 µg/ml to 25 µg/ml of the compound of formula (II), in relation to the volume of the tooth filling material or dental varnish.

15. Tooth filling material or dental varnish according to claim 2, wherein the one polymerisable monomer or one, two, three, a plurality of or all the plurality of polymerisable monomers of the component (b) is/are selected from the group consisting of ethylene glycol dimethacrylate (EGDMA), 1,6-hexanediol dimethacrylate (HEDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, triethylene glycol dimethacrylate (TEGDMA), urethane dimethacrylate (7,7,9-trimethyl-4,13-dioxo-3,14-dioxa-5,12-diazahexadecan-1,16-dioxy-dimethacrylate (UDMA)), glycerol dimethacrylate (GlyDMA), bisphenol-A-glycidyl-methacrylate (Bis-GMA), 1,12-dodecandiol dimethacrylate (DODMA), hydroxyethyl methacrylate (HEMA), polyethylene glycol dimethacrylate (PEGDMA) and ethoxylated bisphenol-A-dimethacrylate (EtoBG).

* * * * *